United States Patent [19]

Brockschmidt et al.

[11] 4,074,561
[45] Feb. 21, 1978

[54] MEANS FOR MEASURING THE PLASTICITY OF COAL

[75] Inventors: Willis H. Brockschmidt, Downers Grove; Robert W. Brockschmidt, Lisle; John D. Grabenhofer, Addison, all of Ill.

[73] Assignee: Fuel Research & Instrument Co., Villa Park, Ill.

[21] Appl. No.: 741,790

[22] Filed: Nov. 15, 1976

[51] Int. Cl.² .......................................... G01N 25/04
[52] U.S. Cl. .................................... 73/17 R; 73/101
[58] Field of Search ................. 73/17 R, 59, 87, 101, 73/15.4; 324/175

[56] References Cited

U.S. PATENT DOCUMENTS

| 3,436,655 | 4/1969 | Lundgreen | 324/175 |
| 3,814,934 | 6/1974 | Mesh et al. | 324/175 |

OTHER PUBLICATIONS

American Society for Testing Materials, Plastic Properties of Coal by the Constant-Torque Gieseler Plastometer, pp. 492–497, 9/24/71.

Primary Examiner—Anthony V. Ciarlante
Attorney, Agent, or Firm—Kinzer, Plyer, Dorn & McEachran

[57] ABSTRACT

A device for measuring the plastic characteristics of coal includes a bath of molten metal and a crucible with a coal sample therein positioned within said bath. A drive motor is connected through a hysteresis brake to a stir rod positioned in the coal sample. As the coal sample plasticizes due to heat from the molten metal, a calibrated disc connected to the stir rod will be driven by the motor. Optical sensing means including a phototransistor and a light source positioned on opposite sides of the calibrated disc are connected to a counter which is used to record stir rod movement within a given time reference.

5 Claims, 4 Drawing Figures

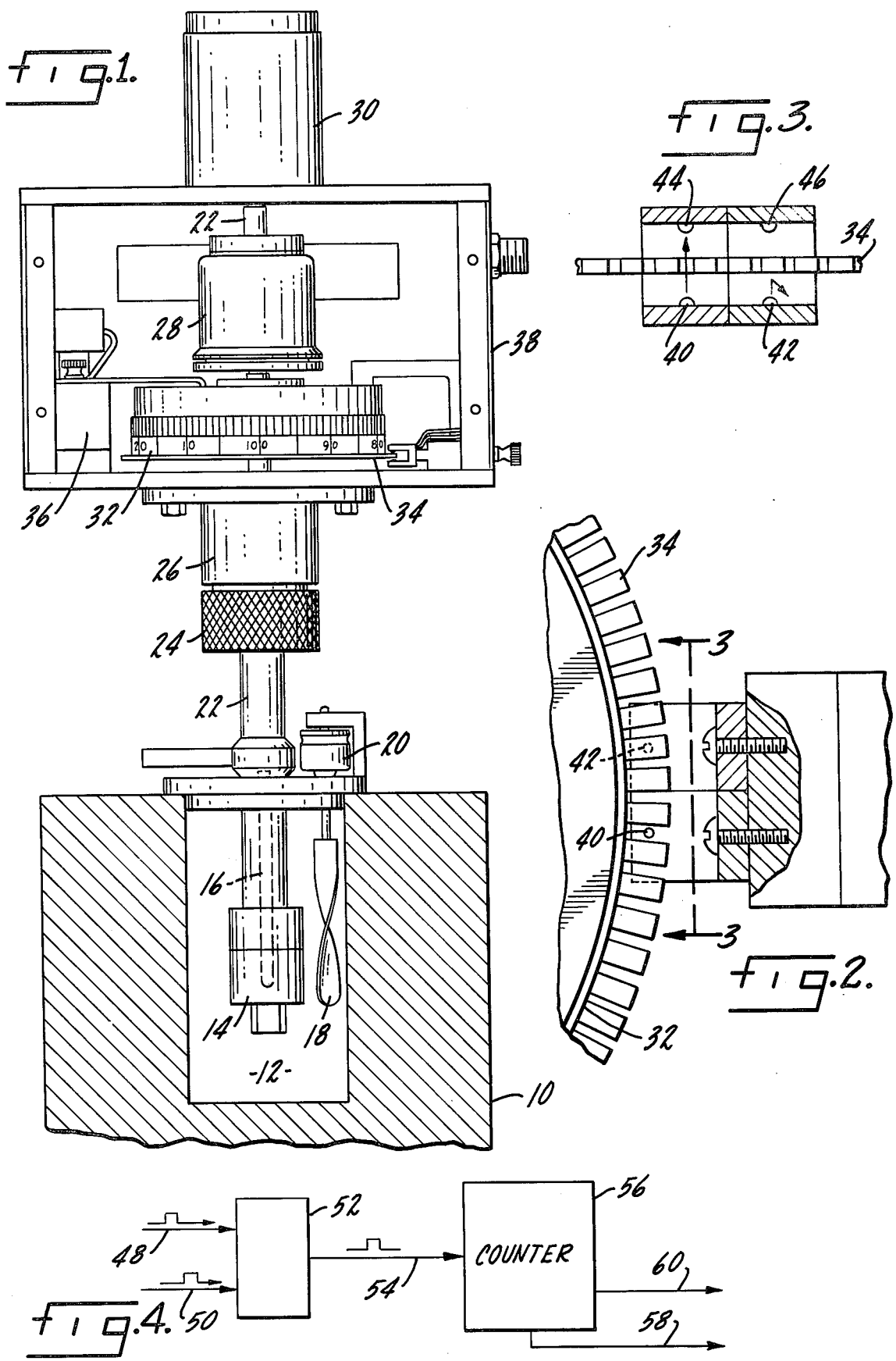

ary of the invention

MEANS FOR MEASURING THE PLASTICITY OF COAL

SUMMARY OF THE INVENTION

The present invention relates to a device for measuring the plastic characteristics of coal and has particular relationship to a means for automatically measuring such plasticity.

A primary purpose of the invention is a means for accurately and automatically recording movement of a calibrated disc operatively engaged with a driven stir rod positioned within a coal sample.

Another purpose is a coal plastic measuring device including a slotted disc attached to a stir rod positioned in a coal sample, and a pair of optical sensing means positioned adjacent the slotted disc, said optical sensing means providing inputs to a flip-flop circuit with the result that a pair of inputs to the flip-flop circuit provides a single output representative of a degree of movement of the slotted disc.

Another purpose is a reliably operable method of measuring rotation of a stir rod positioned within a coal sample heated by a bath of molten metal.

Other purposes will appear in the ensuing specification, drawings and claims.

BRIEF DESCRIPTION OF THE DRAWINGS

The invention is illustrated diagrammatically in the following drawings wherein:

FIG. 1 is a plan view, in part section, of a plastometer of the type described,

FIG. 2 is an enlarged top plan view of a portion of the optical sensing means,

FIG. 3 is a section along plane 3—3 of FIG. 2, and

FIG. 4 is a partial diagrammatic illustration of the electrical circuitry used herein.

DESCRIPTION OF THE PREFERRED EMBODIMENT

The present invention relates to plastometers for measuring the plastic characteristics of coal, such instruments being known in the trade as Gieseler plastometers. Instruments of this type have been used to measure the plastic characteristics of coal for a number of years and are described in detail in ASTM Designation D 2639-67T. The specification herein will only describe the plastometer in general terms.

In FIG. 1 a controllable furnace is indicated generally at 10 and a bath pot 12 is positioned therein. The bath pot may contain a lead or a solder in melted form with the temperature of the bath pot being carefully controlled and regulated by furnace 10.

Positioned within the molten metal in bath pot 12 is a crucible 14 having a coal sample to be tested packed therein. A stir rod 16 extends into the crucible and will be driven as described hereinafter. A stirrer or paddle 18 is positioned within the molten metal in bath pot 12 and will be driven through a drive pulley 20. The paddle 18 provides uniform distribution of heat within the bath pot and thus an evenly applied temperature for the crucible.

An axle 22 is connected to stir rod 16 and extends through a coupling nut 24 and a bearing housing 26 to a hysteresis brake 28. A drive motor 30 is connected to the upper end of axle 22 with the result that the drive motor drives axle 22 and thus stir rod 16 with a force determined and controlled by hysteresis brake 28. The structure described above is conventional and known in the art.

Attached to axle 22 is a calibrated disc 32 and a slotted disc 34. A revolution counter 36 is positioned along one side of the plastometer head assembly 38 and is arranged to record and count the number of revolutions of disc 32.

In the operation of the plastometer, a coal sample is packed within the crucible and the crucible is lowered into the bath pot which is positioned within the furnace. The furnace is electrically heated and may contain a solder bath which is capable of being increased in temperature at a rate of 3° C. per minute. A controller will automatically increase the temperature of the bath at the required rate. The torque applied to stir rod 16 is controlled by hysteresis brake 28 and a torque of 40 gram inches is conventionally used as the rotating force applied to the stir rod.

Coking coals soften and become plastic as they pass through the temperature interval in being converted from coal to coke. The plastometer measures the initial temperature at which the coal softens, the maximum fluidity, when there is maximum movement of calibrated disc 32, and the final temperature at which the coal solidifies. The range of plasticity is the degrees of temperature between the initial temperature and the final temperature. The fluidity as well as the temperature range are essential in the selection of coals for carbonization.

Positioned on one side of slotted disc 34 are a pair of spaced infrared light sources 40 and 42. Positioned on the opposite side of the disc are a pair of phototransistors 44 and 46. As shown particularly in FIG. 3, the relative peripheral positioning of the phototransistors and their light sources and the spacing between slots in disc 34 is such that only one phototransistor will receive a light pulse at any given instant. This arrangement is also illustrated diagrammatically in FIG. 2.

The output pulses from phototransistors 44 and 46 are diagrammatically illustrated on lines 48 and 50 as being applied to a JK flip-flop circuit 52. After input pulses from both phototransistors flip-flop 52 will provide an output pulse on line 54 to a counter 56. There are two outputs from counter 56, one output being on line 58 providing a timing signal, with the output on line 60 going to a printer readout which will illustrate in usable form the number of dial divisions per minute of movement of calibrated disc 32 which in turn is a direct indication of the plastic characteristics of the heated coal within the crucible. This information will be displayed in a visual manner either on a printer or on a digital display device in conjunction with a printer.

Of importance in the invention is the accurate means for determining the number of dial divisions of movement in a given time frame. The use of two sensors and two pulses compensates for slight irregularities in movement of the disc as at times, prior to actually beginning movement as the coal plasticizes, there can be some jitter or back-and-forth movement of the stir rod and thus the disc. The recording of such incorrect movement is eliminated by the use of a pair of optical sensing devices connected in the manner shown through a flip-flop circuit.

Whereas the preferred form of the invention has been shown and described herein, it should be realized that there may be many modifications, substitutions and alterations thereto.

The embodiments of the invention in which an exclusive property or privilege is claimed are defined as follows:

1. A means for measuring the plastic characteristics of coal including a bath of molten metal, a crucible with a coal sample therein positioned in said bath, a stir rod in said coal sample and a drive motor for said stir rod, and means for measuring movement of the stir rod as the coal plasticizes, including a calibrated disc having a uniformly slotted periphery operatively engaged for rotation with said stir rod, means for counting the number of revolutions of said calibrated disc, optical sensing means positioned adjacent said disc, including a pair of spaced light sources positioned on one side of said slotted periphery and a pair of spaced phototransistors, in alignment with said light sources and positioned on the opposite side of said slotted periphery, and a counter connected to said optical sensing means for recording stir rod movement within a given time reference.

2. The means of claim 1 further characterized in that said light sources are infrared.

3. The means of claim 1 further characterized in that said phototransistors are connected to a flip-flop circuit, with the output of said flip-flop circuit being connected to said counter, said flip-flop circuit providing a single output pulse after receipt of input pulses from both of said phototransistors.

4. The means of claim 1 further characterized by and including a brake connected between said drive motor and stir rod for controlling the amount of torque applied by the drive motor to said coal sample.

5. The means of claim 1 further characterized by and including means for agitating said molten metal bath to maintain a uniform temperature therein.

* * * * *